United States Patent
Bookwalter et al.

(10) Patent No.: US 6,530,883 B2
(45) Date of Patent: Mar. 11, 2003

(54) SURGICAL RETRACTOR ASSEMBLY

(75) Inventors: John R. Bookwalter, Brattleboro, VT (US); Rene J. Cabrera, Stoughton, MA (US); Wesley C. Walker, Marion, MA (US); Kenneth R. Hayes, Fall River, MA (US)

(73) Assignee: Codman & Shurtleff, Inc., New Brunswick, NJ (US)

( * ) Notice: Subject to any disclaimer, the term of this patent is extended or adjusted under 35 U.S.C. 154(b) by 0 days.

(21) Appl. No.: 09/872,672

(22) Filed: Jun. 1, 2001

(65) Prior Publication Data

US 2002/0026101 A1 Feb. 28, 2002

Related U.S. Application Data

(63) Continuation of application No. 09/413,949, filed on Oct. 6, 1999, now Pat. No. 6,241,659.

(51) Int. Cl.$^7$ ................................................. A61B 1/32
(52) U.S. Cl. ...................................... 600/231; 600/233
(58) Field of Search ................................ 600/201, 210, 600/213, 226, 227, 228, 231, 232, 233, 234, 204, 205, 209, 225, 229

(56) References Cited

U.S. PATENT DOCUMENTS

| | | | |
|---|---|---|---|
| 3,384,078 A | * | 5/1968 | Gauthier |
| 3,749,088 A | | 7/1973 | Kohlmann |
| 3,965,890 A | | 6/1976 | Gauthier ..................... 600/233 |
| 4,254,763 A | | 3/1981 | McCready et al. |
| 4,421,108 A | | 12/1983 | Cabrera et al. |
| 4,424,724 A | | 1/1984 | Bookwalter et al. ........... 74/540 |
| 4,467,791 A | | 8/1984 | Cabrera et al. |
| 4,813,401 A | | 3/1989 | Grieshaber ................... 600/231 |
| 4,949,707 A | | 8/1990 | LeVahn et al. .............. 600/234 |
| 5,052,373 A | | 10/1991 | Michelson |
| 5,280,782 A | | 1/1994 | Wilk |
| 5,375,481 A | | 12/1994 | Cabrera et al. ................ 74/577 |
| 5,512,038 A | | 4/1996 | O'Neal et al. ............... 600/210 |
| 5,514,075 A | * | 5/1996 | Moll et al. ................... 600/202 |
| 5,520,608 A | | 5/1996 | Cabrera et al. .............. 600/201 |
| 5,616,117 A | | 4/1997 | Dinkler et al. ............... 600/232 |
| 5,893,831 A | | 4/1999 | Koros et al. ................. 600/232 |
| 5,908,382 A | | 6/1999 | Koros et al. ................. 600/232 |
| 5,944,736 A | | 8/1999 | Taylor et al. ................ 600/198 |
| 5,947,895 A | * | 9/1999 | Warner ........................ 600/204 |
| 5,947,896 A | * | 9/1999 | Sherts et al. ................. 600/229 |
| 6,206,826 B1 | * | 3/2001 | Mahews et al. ......... 600/221 X |
| 6,241,659 B1 | * | 6/2001 | Bookwalter et al. ......... 600/231 |

FOREIGN PATENT DOCUMENTS

DE     41 18 220     11/1992     ........... A61B/17/02

* cited by examiner

Primary Examiner—Jeffrey A. Smith
(74) Attorney, Agent, or Firm—Nutter McClennen & Fish LLP

(57) ABSTRACT

A retractor systems includes a retractor blade with a blade portion and a handle portion that fit together in a modular way to allow different blades to be removably and interchangeably affixed to the handle assembly. A dovetail mounts the blade in a plane substantially transverse or perpendicular to the shaft. Preferably, the handle assembly translates within a multi-position locking mechanism to allow adjustment of the handle extension along one or more axes, while the in-plane swing of the blade about the shaft conveniently positions the tip of the blade under tissue to be retracted when bone or hard tissue may impede access along a retraction direction parallel to the axis of the shaft. The interchangeable blades may have different sizes between approximately 5 and 15 centimeters length, and are manually affixed to the handle to set the reach and scope of the retractor for a particular operation. Preferably a blade is formed of a radiolucent polymer, permitting unobstructed imaging when the retractor is occluded during surgery on a joint, or during an anterior approach to the spine. The blade may be formed with its surface dished or curved in one or more directions, or may have a lip or flare adapted for a contacting or retracting a particular tissue or structure. The surface of the blade swings down to engage muscle along a path substantially tangent to a hard tissue structure or bone from which the tissue is to be retracted.

11 Claims, 5 Drawing Sheets

SURGICAL RETRACTOR ASSEMBLY

CROSS-REFERENCE TO RELATED APPLICATIONS

This application is a continuation of U.S. patent application Ser. No. 09/413,949 filed on Oct. 6, 1999, now U.S. Pat. No. 6,241,659.

STATEMENT REGARDING FEDERALLY SPONSORED RESEARCH

Not Applicable.

BACKGROUND OF THE INVENTION

The present invention relates to a surgical retractor assembly and more particularly to a retractor assembly useful in surgery involving bones or hard tissue structures, such as in spine or joint surgery.

In many surgical operations it is customary to employ a retraction apparatus in which a frame or mounting ring rests over the patient surrounding the surgical opening, and a number of retractors may be movably attached to the frame and flexibly positioned, with various clamping or positioning mechanisms, to reach into the surgical opening and retract surrounding or obstructing tissue or organs, or to stabilize or position tissue or organs that are being worked on. In general, such retractors may include a blade or spoon-like member, or various gripping members, that each extend from an elongated handle or stem, and the stem moves within a clamping mechanism that mounts on the mounting ring and locks the blade or gripping member in a selected position. The clamping mechanism may itself have a mechanical structure allowing one or more additional degrees of movement in rotation or displacement, so that both the position and orientation of the blade may be quickly set and locked. Various common machine elements such as swivel ball mounts, arcuate rack or tilt mounts, rachet or rack adjustment and locking mechanisms, or screw clamps may be incorporated in the clamping structures to provide assemblies that are moved by hand into the desired position and locked.

By way of example, one commercially useful system is shown in the various patents of John R. Bookwalter, et al. such as U.S. Pat. Nos. 4,424,724; 4,254,763; 4,421,108; 5,375,481; and 5,520,608. This system is made and marketed by Codman. In the Bookwalter system, the frame element is a flat ring with regular notches. The ring is held by a post that clamps to the side rail of the operating table, so the ring is suspended in a plane above the surgical site. The plane of the ring sets one constraint on the movement of the retractor units, and allows the various retractor clamp assemblies to move into position and lock with a sliding movement that is conveniently set with one hand.

Many other surgical equipment suppliers also make surgical retractor systems, which may, for example be distinguished by one or more novel blades, clamps or frames, by a dimension or shape adapting the system to a particular surgery, or by features such as a round clamping ring or linked ring segments, to achieve their positioning and retracting abilities.

In general, such systems are intended to efficiently perform their function of retracting or positioning tissue in the surgical arena in a manner that allows simple adjustment with few motions by the surgeon during the course of a procedure, and without interfering with or obstructing the access lines necessary for manipulation within the surgical arena. In effect, a surgical retractor system requires a high degree of versatility to reach to and to retract or reposition, various tissues or organs as the surgical procedure proceeds. To a large extent, when it is simply a question of retracting soft tissue structures during abdominal or thoracic surgery, the required tasks can be performed with a set of just a few contoured blades having various lengths that extend proximate to the surgical opening as shown in the aforesaid patents. However, when the tissue does not consist of soft organs or structures spaced about a large opening but instead requires retraction of muscle or connective tissue from bony structures, the alignment of the blade with the tissue becomes more difficult, and it may be awkward to correctly insert or align the available clamping structures and retraction blades with the intended tissue. This is especially true for operations in and around bones and joints.

Accordingly, it would be desirable to develop an improved surgical retractor blade.

It would also be desirable to develop a surgical retractor system useful for surgery on bones and joints.

It would also be desirable to develop a surgical retractor system useful for spinal surgery.

It would further be desirable to develop such a retractor blade which is also usable with existing clamps and rings.

SUMMARY OF THE INVENTION

One or more of the above desirable features are obtained with a basic embodiment of the present invention by providing a retractor blade with a controlled degree of self rotation such that the blade swings into alignment near a bone or hard tissue structure. The retractor blade includes a blade portion and a handle portion which may for example be integrally joined or may fit together in a modular way to allow different blades to be removably and interchangeably manually inserted into the handle assembly. The handle assembly in turn is configured so its stem slides back and forth within a ratcheting or similar multi-position locking mechanism to allow adjustment of the stem extension along one or more axes, and is rounded to effect a limited range of angular rotation of the blade about the stem axis.

In a preferred embodiment the retractor stem has a rounded cross-section of substantially circular shape with one or more protruding ridges extending along the axial direction such that the edge-to-edge thickness of the stem varies with angular position about the axis, from a free to a jammed state. The handle is configured to slide back and forth within a ratchet clamp mechanism and has a rack, thread or other stepped surface such that when inserted through the clamp mechanism a spring loaded pawl or locking lever locks the handle at a defined extensional length. Preferably, the ridges of the handle are equi-spaced around its circumference, and fit within a square passage such that the ridge-to-ridge stem diameter is greater than the width of the square channel and is less than its diagonal. As a result, the handle may rotate freely about its axis by an amount less than $\pi/4$, up to a point at which the ridges jam by interference against the walls of the passage. Preferably four ridges are spaced at 90° intervals around the circumference, and are dimensioned such that the handle, when fitted through a conventional square passage clamp assembly rotates up to about 30° to either side before jamming. The interference contact of ridges and wall thus limits the ability of the blade to swing sideways more than a limited amount, while allowing free movement as necessary for the surface of the blade to swing tangentially down to a position close to a hard tissue structure or bone, and to precisely reach and retract tissue, such as muscle or connective tissue, from the immediate vicinity thereof Most preferably, the ridges have an asymmetric ramp or slope, having a graded ascent with a sharp drop off after the peak, thus providing a smooth resistance up to the point of jamming, and well controlled release when it is necessary to remove the blade.

In a preferred embodiment the retractor blade assembly comprises a handle and a blade. The handle has a stem with a blade mounting block assembly secured to the end of the stem. The stem extends along an axis and the blade mounting block has a dovetail channel extending transverse to the axis. The blade is formed as a separate element, and is manually inserted into the mounting block to complete the retractor. Both the stem and the block are formed of a material such as stainless steel, while the blade may be formed of a material such as a suitable nylon, polyethylene or polycarbonate typically having lesser hardness or stiffness modulus, and suited as a disposable or single-use item. The proximal end of the blade has a shape matching the dovetail channel of the handle assembly, and is configured to manually press fit securely into the dovetail channel. Blades of different sizes between approximately 5 and 15 centimeters length are provided in a modular set so that a retractor blade may be selected and assembled during surgery to achieve the desired reach and scope of use for a particular retraction. Preferably the blade is formed of an unfilled polymer which is translucent to radiographic imaging energy, thus permitting unobstructed images to be made with the retractor in place. This embodiment is particularly advantageous for operations such as anterior approaches to the spine, or for operations such as joint surgery, where a view of the blade is occluded from one or more aspects.

The blade may be formed with its surface dished or curved in one or more directions, or may have a lip or flare adapted for penetrating or retracting a particular structure, such as tissue contacting the spine. The dovetail is configured such that the blade itself mounts in a plane substantially transverse or perpendicular to the retractor shaft. Rotation of the shaft then allows the blade to swing into different angular orientations within the plane of the blade, while the tip of the blade changes its vertical height or offset from the mounting ring. This is particularly advantageous for bringing the curved tip of the blade down under a cut edge of tissue in an essentially planar approach to retract the tissue from a bone, where blade movement parallel to the shaft axis would be impeded by the bone.

BRIEF DESCRIPTION OF THE DRAWINGS

These and other features of the invention will be understood from the description and claims herein, taken together with drawings of illustrative embodiments, wherein:

DETAILED DESCRIPTION

Figure 1:
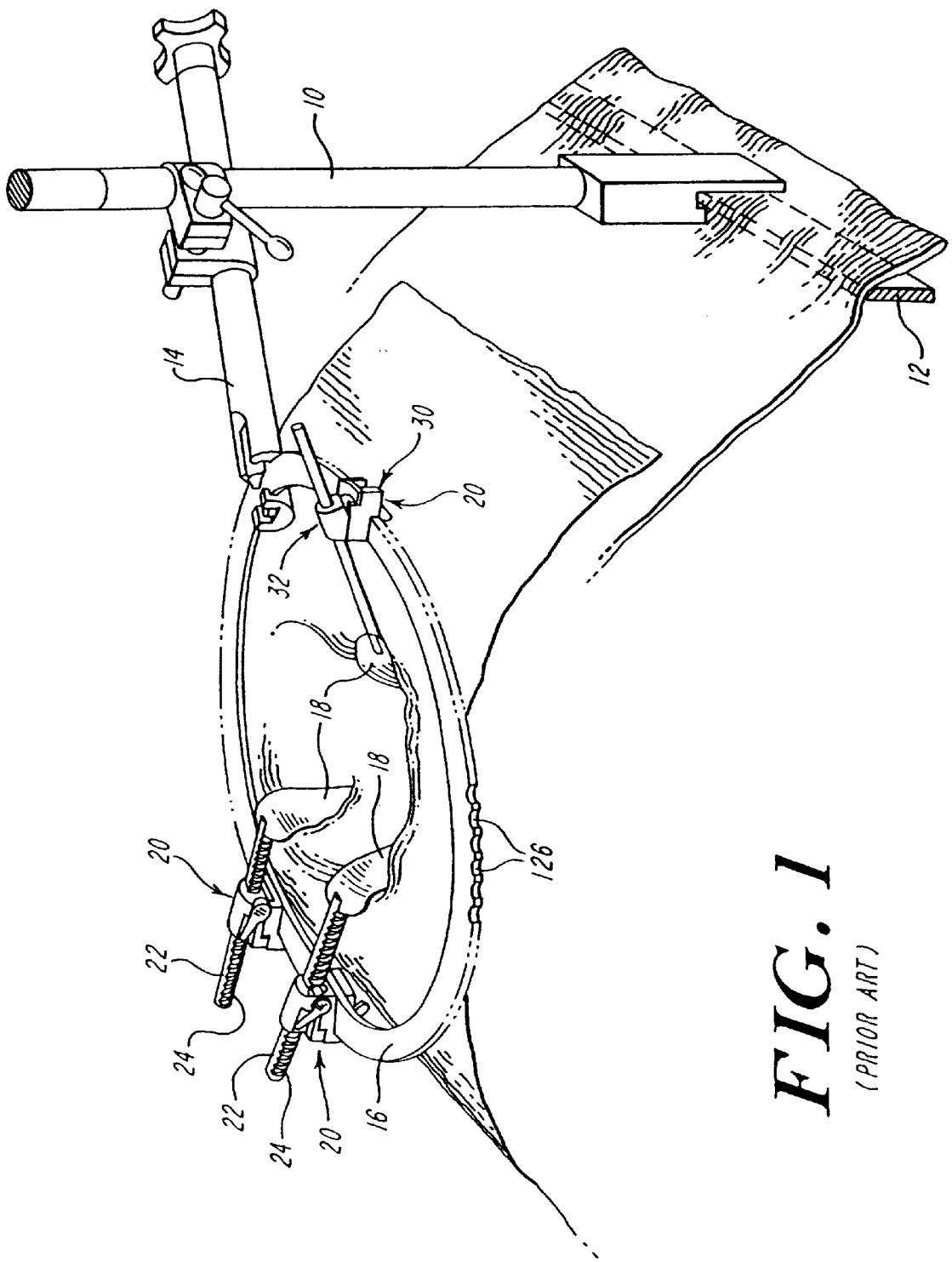
FIG. 1 shows a general perspective view of a representative retractor system of the prior art usable with retractor blades of the present invention.

FIG. 1 shows a surgical retractor assembly which may, for example, be similar to that shown in U.S. Pat. No. 5,375,481. A vertical support post 10 is clamped to the side rail 12 of an operating table on which the patient is supported. An arm 14 extends horizontally over the patient and supports a support ring 16 on which a number of retractor blades 18 are carried by respective ratchet locking mechanisms 20. Each retractor blade 18 includes a long shaft or stem 22 along one side of which is included a rack or ratchet track 24. Retractor blades 18 extend into the surgical opening for retracting tissue. The clamping or ratchet mechanisms 20, are configured to fix the position on the ring 16 as well as to set the extension and or angle, of the retractor blades 18, with one or more simple clamping motions. In the prior art such clamping or ratchet mechanisms have included ones with a square passage for accommodating a shaft of a retractor blade in a fixed orientation about its shaft, and ones with a round passageway for accommodating notched or threaded cylindrical shafts that permit the retractor blade to be rotated in an arbitrary position. The detailed construction of several suitable ratchet mechanisms is set forth in U.S. Pat. No. 5,375,481 and in U.S. Pat. No. 4,424,724. These mechanisms allow the surgeon to retract and lift an organ at the same time as they duplicate the natural toe-in or angular retraction one achieves by hand.

The present invention seeks to provide a convenient retractor blade assembly, preferably adapted for use with the ratchet clamp assemblies of the above cited prior art systems, which is efficiently and conveniently used to retract tissue from bones for various bone, spine and joint surgery. As shown more fully in FIG. 2, in accordance with a principal aspect of the present invention the retractor blade assembly 300 is provided with a stem or handle portion 310, that fits within a generally rectangular bore 42 and is adapted to ratchet and lock its position therein. The multi-position ratchet mechanism 20 may be generally identical to those of the prior art and, as illustrated, preferably includes a ratchet tilt mechanism 32 pivotally attached by means of a pin 34 extending through bores 36 and 38 in a ratchet holder 30, and through a bore 40 in the ratchet pivot housing 32. A generally rectangular bore 42 extends completely through the pivot housing 32 to receive the retractor blade shaft or stem 310 as shown in more detail in the following figures. However, in accordance with a principle aspect of the present invention, unlike the passageway 42, the stem itself is generally rounded or cylindrical, and possesses one or more, and preferably several protruding lobes 311 which allow it to undergo a partial rotation within the bore or passage 42. Thus, the retractor blade stem is a rounded stem adapted to fit a square hole.

Figure 2:
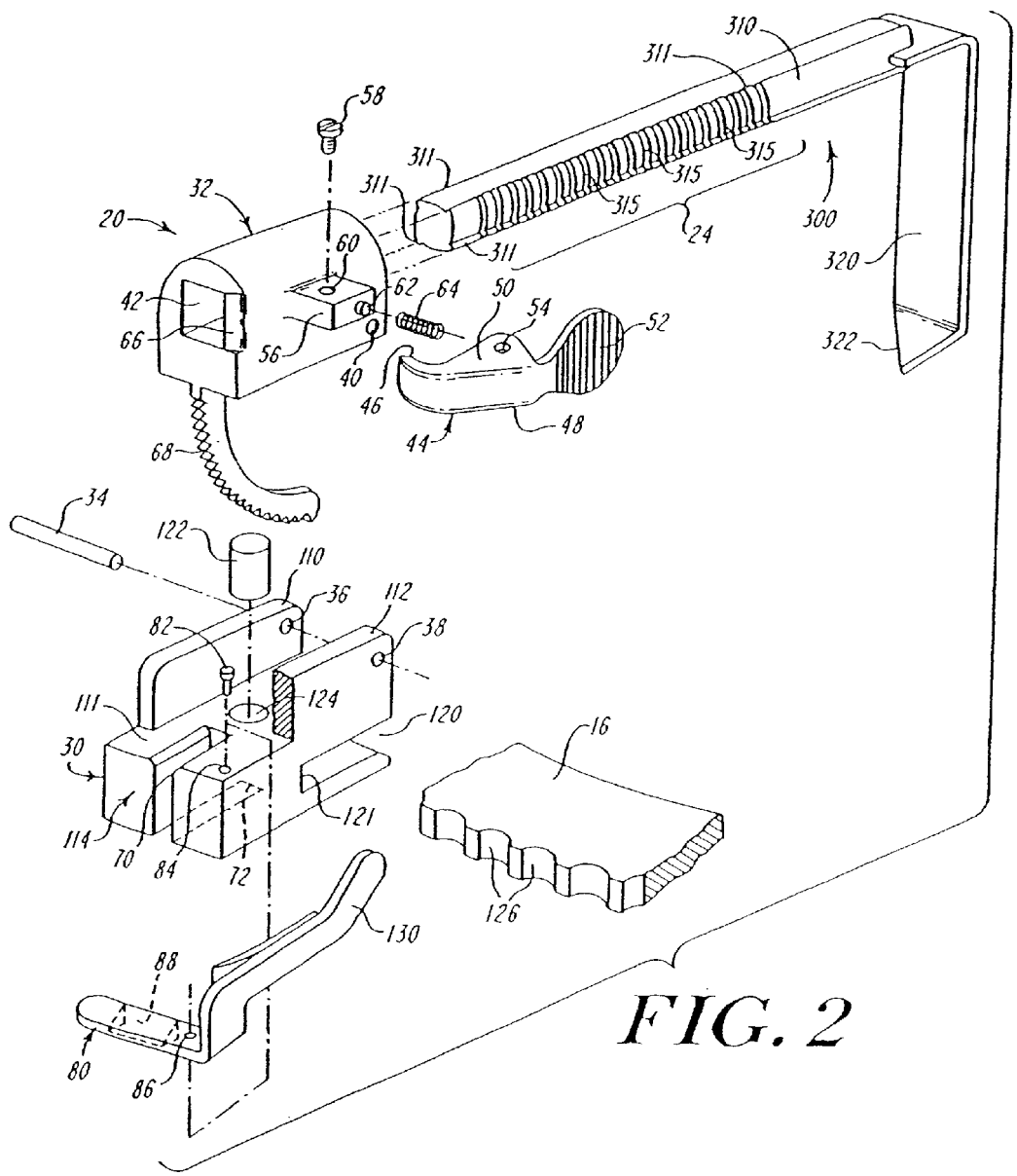
FIG. 2 shows a clamp assembly of the system of FIG. 1 with a retractor blade of the present invention.

As further shown in FIG. 2, the stem 310 further has a rank of notches 315 extending along one side of the stem, and aligned to form a rack 24 disposed on one side of the retractor blade stem 310. A retractor pawl 44, which includes a pawl blade 46, left and right skirts 48, 50 and an actuating surface or thumb-piece 52, engages the rack 24. Each of the skirts 48 and 50 includes a bore 54. The retractor pawl 44 is mounted to a boss 56 extending from the side of the ratchet pivot housing 32, by means of a screw 58 which projects through the bores 54, and through the bore 60 in the boss 56. Boss 56 further supports a bias spring 64 on a projecting nub or pin 62 for biasing the retractor pawl blade 46 into close engagement with the rack 24 on the side of the retractor blade stem 310. A corner 66 of the ratchet pivot housing 32 is beveled or cut away to provide clearance for the pawl blade 46 to fully engage the notches of the rack 24.

In the illustrated holder assembly a curved rack 68 depends from the bottom of the ratchet pivot housing 32 toward the ratchet holder 30. The rear surface 114 of the ratchet holder 30 includes a vertical slot 70 which receives the curved rack 68. The interior transverse wall 72 of the slot 70 is curved to the same radius as the tilting rack 68 so that the rack 68 may slide easily and precisely of the slot 70 as the pivot housing 32 tilts around the pin 34.

As further shown in FIG. 2, the retractor blade assembly includes a blade portion 320 which extends transversely to the stem 310 and has a distal end with a rake tip 322 that angles down and outwardly, back toward the surrounding mounting ring 16. This blade is particularly adapted to retracting tissue from bones. The length of the blade may vary, and in a preferred embodiment is configured for retracting tissue, for example, from the spine in an anterior approach through the peritoneal cavity, where the blade must reach down to retract tissue close to bone and at a depth near the floor of the surgical opening.

The lower portion of the illustrated rachet clamping assembly is particularly adapted to Bookwalter mounting system ring 16 and is fully described in the aforesaid U.S. Pat. No. 5,275,481. Generally the top surface 111 of the ratchet holder 30 includes left and right side walls 110 and 112 which extend along the ratchet holder 30. The side walls 110, 112 are spaced apart a sufficient distance to permit the ratchet pivot housing 32 to pivot between them, with a small clearance, so as to provide lateral stability to the ratchet pivot housing. The sidewalls 110 and 112 extend along the top surface of the ratchet holder for a distance equal to the length of the ratchet pivot housing 32. The holder 30 includes a transverse slot 120 which permits the ratchet holder 30 to slide onto the support ring 16 shown in FIG. 1. Slot 120 extends from the front face of the ratchet holder 30 toward the rear face, a distance less than the width of ring 16. A dowel pin 122 fits with a tight fit into a bore 124 such that the circumferential edge of the dowel pin 122 projects into the slot 120. When the ratchet holder 30 is placed onto the ring 16, the circumferential edge of the dowel pin 122 engages one of the indentations 126 on the outer edge of the ring 16 to fix the circumferential position of the ratchet holder 30 on the ring 16. Alternatively, a rounded projection molded or cast in the rear wall 121 of slot 120 may be substituted for the bore 124 and pin 122. In each case, tension of the retractor blade against the retracted tissue pulls the retractor holder forward so that the projection, or the edge of the dowel pin 122, engages the indentations 126 on the ring 16 to prevent circumferential slipping of the ratchet holder 30 and to prevent the ratchet holder 30 from pulling off the ring 16. A release bar 80 is further affixed to the top surface of the illustrated ratchet holder 30 adjacent the slot 70. The ratchet release bar 80 is affixed by a pin 82 which extends through a hole 86 and is retained in a bore 84 in the body of the ratchet holder. The ratchet release bar has a thumb piece 130 generally formed in an L-shape, with a cut out portion 88 on one side of the ratchet release bar to engage with the rack a 68, on the ratchet pivot housing 32. When the cut-out portion 88 engages the teeth in the curved rack 68, the ratchet pivot housing is fixed in its tilt orientation. Operation of the ratchet holder and pivot assembly is described more fully in the aforesaid patents.

Figure 3:
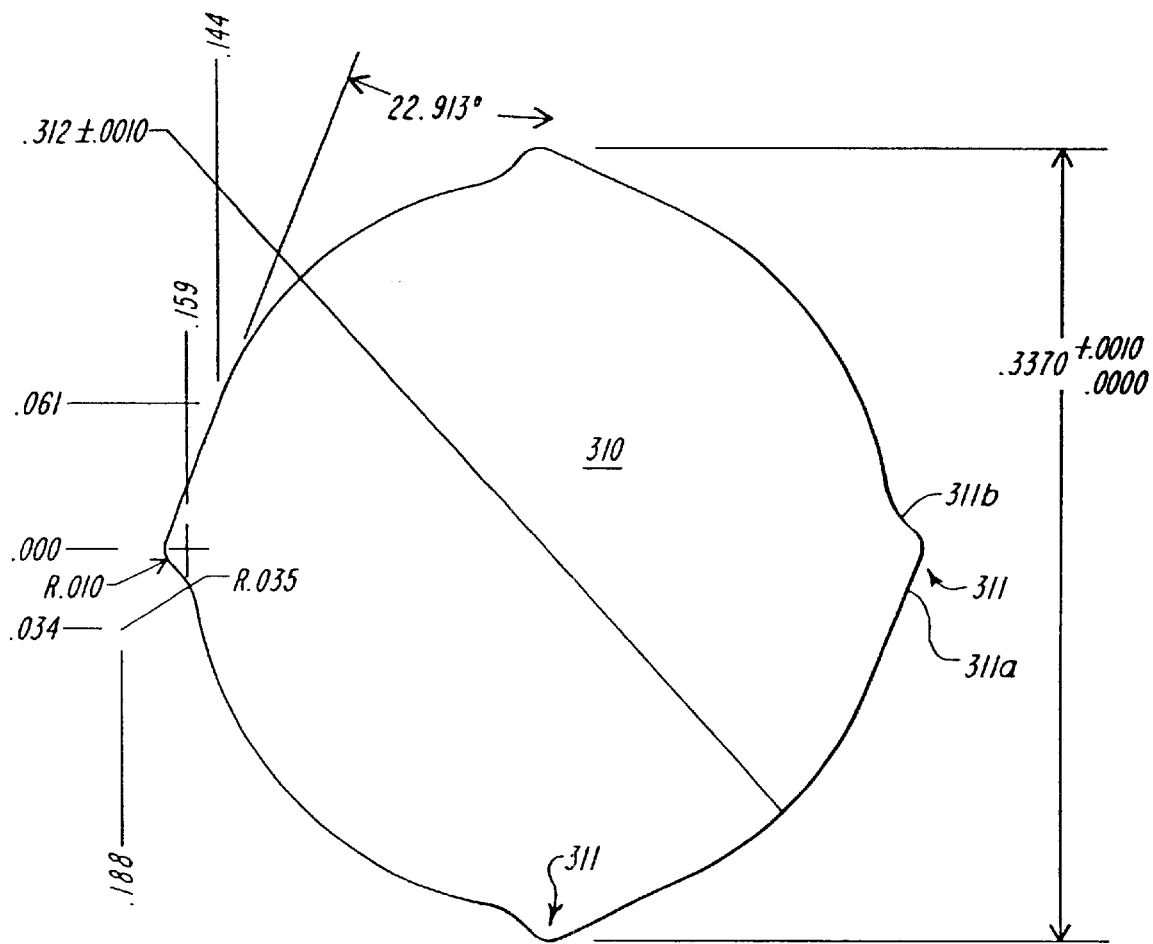
FIG. 3 is an enlarged sectional view of the stem of FIG. 2.

FIG. 3 shows an enlarged sectional view of the stem 310 of the retractor blade of FIG. 2. As shown, the stem is in an elongated rod of generally cylindrical shape illustratively with a diameter of 0.312 inches, and possesses four equi-spaced lobes 311 positioned at 90 degree intervals around the circumference which each protrude outwardly approximately 0.012 inches, so that the diameter between opposed lobes is somewhat larger, e.g., 0.337 inches in the illustrated embodiment. Each lobe 311 has a radiused peak, and is configured with a gentle ramp 311 a illustratively of about 23° approaching one side, followed by a relatively abrupt and recessed or relieved drop off 311b sloping down from the other side. The stem may be made by drawing steel rod stock through a die having an aperture of corresponding shape, to produce lobed rod stock in lengths, for example, of several meters, and then grinding or otherwise machining the stock to the indicated profile, and cutting to suitable lengths. The length of the stem portion for each retractor handle assembly may be approximately eight inches (twenty centimeters). Blade attachment may be effected by milling a slot in one end of the rod and brazing or silver soldering a blade in the slot, or attachment may be effected by other means.

Figure 4:
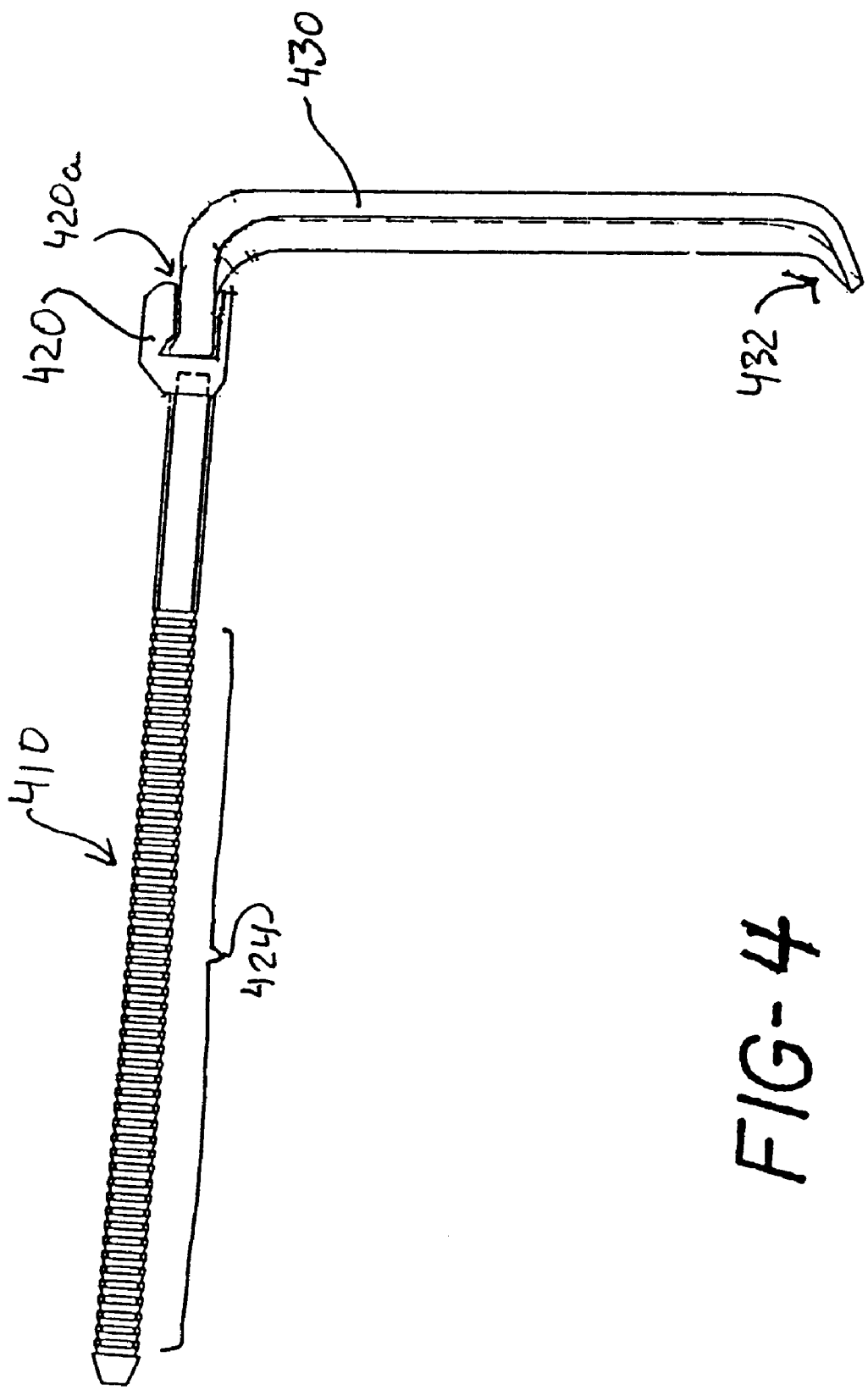
FIG. 4 illustrates another embodiment of a retractor blade of the invention.

In accordance with a further aspect of the invention, the blades for the assembly consist of a set of manually insertable and interchangeable blades of differing length or shape each adapted to attach to a common, separate, handle assembly. One embodiment of this aspect of the invention is illustrated in FIG. 4. In accordance with this aspect of the invention, the retractor blade assembly includes a stem 410 with a blade holder 420 at its distal end and a separate blade 430 adapted for removable insertion in the holder 420. The stem 410 is substantially identical to the stem 310 described above, while the holder 420 consists of a solid block permanently affixed, for example by electron beam welding, to the stem 410 and having a transverse dovetail groove 420A extending therethrough. As in the previously discussed embodiment, the stem 410 includes protruding lobes configured to gently jam in rotational position within the square bore of the clamp assembly, and includes a rack 424 disposed generally along one side of the stem for engagement with the ratcheting pawl assembly of the clamp.

The removable and replaceable blade 430 is preferably formed of a radiolucent polymer of suitable thickness, and except for this somewhat enlarged thickness, may have a contour similar to that of any known metal retractor blade, with a concave or convex curvature with respect to one or more axes to form a generally shoe-horn, spoon-, dished or other shaped surface. The curvature further adds stiffness against bending along the longitudinal and/or transverse axes. As with the embodiment described above, the blade 430 preferably includes a toed-in distal tip 432 to fit under or behind tissue and prevent slippage.

Figure 5:
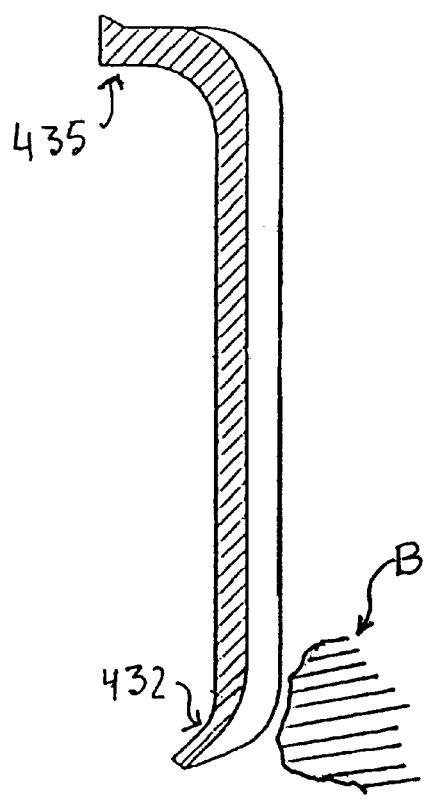
FIGS. 5 and 6 illustrate the blade portion of the preferred embodiment of FIG. 4.
Figure 6:
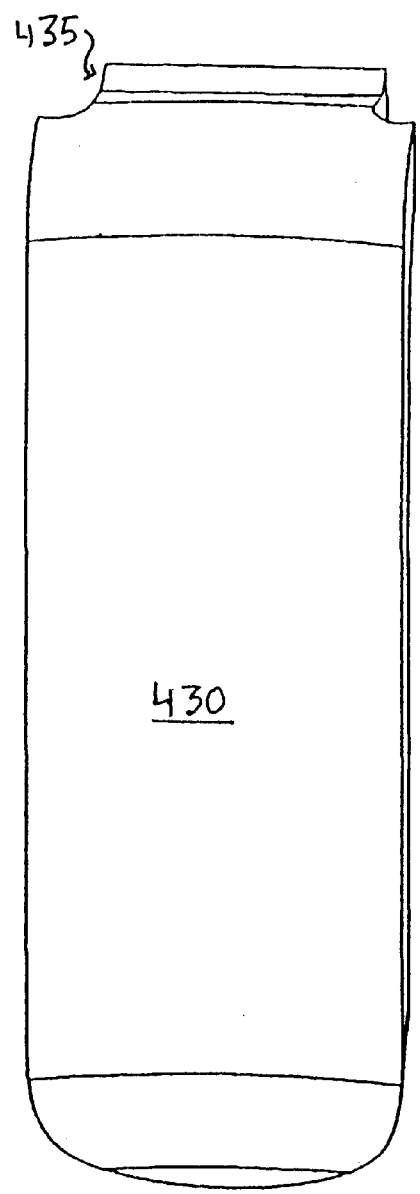

FIGS. 5 and 6 illustrate respectively, a section through a vertical plane centrally bisecting the blade 430 of FIG. 4, and a schematic front perspective view of the blade. As shown, the blade 430 possesses a generally broad major front face and depends from a thickened dovetail shank 435 which rigidly affixes it in the groove 420a of the mounting block 420 of the handle. The distal tip of the blade 432 curves generally inward and back in a spoon-hook beak of thinned aspect to allow greater flexibility and maneuverability for insertion behind or under a tissue edge, for initial placement of the retractor and to prevent tissue from slipping out once retracted. As shown, the profile is well adapted to having the blade swing down proximate to a bone or other hard tissue B (shown schematically in FIG. 5) along the degrees of motion permitted by the shaft assembly as described above.

The invention has been described above with respect to several representative embodiments, but is not limited to the disclosed implementations. Rather, based on the above-described embodiments, one skilled in the art will appreciate further features and advantages of the invention, and will readily adapt the invention to other retractor mechanisms and components thereof. Thus, basic embodiments and representative implementations of the invention being described, variations and modifications will occur to those skilled in the art, and all such variations and modifications are considered to be within the scope of the invention, as defined by the claims appended hereto and equivalents thereof. All publications cited herein are expressly incorporated herein by reference in their entirety.

What is claimed is:

1. A retractor assembly for positioning tissue in a surgical arena, such retractor assembly comprising:

a clamp having a channel with a non-circular cross-sectional shape;

a shaft adapted for longitudinal movement in the clamp channel and having at least one elongated surface ridge such that the shaft rotates freely within a limited range in said channel for self alignment when contacting tissue, and the shaft jams against the channel by interference of said ridge with said channel to automatically limit a range of rotation of the shaft.

2. The retractor assembly of claim 1, further comprising a retractor blade secured in position by the shaft and clamp to retract patient tissue.

3. The retractor assembly of claim 1, wherein the clamp is adapted to mate to a frame securable proximate to a patient.

4. The retractor assembly of claim 1, wherein the at least one elongate surface ridge on the shaft extends along a length of the shaft.

5. The retractor assembly of claim 4, wherein the shaft includes four equi-spaced elongate surface ridges.

6. A retractor assembly for positioning tissue in a surgical arena, such retractor assembly comprising:

a frame securable proximate a patient;

a shaft adapted for longitudinal movement in a clamp assembly mounted to the frame;

a retractor blade secured by the shaft and clamp in a position to retract patient tissue, the blade having a proximal end, a distal end and an intermediate portion located between said proximal and distal ends; and a mounting block attached to the end of said shaft, said mounting block being configured to removably and replaceably secure the retractor blade;

wherein the proximal end of the blade has a dovetail configured to fit in a grooved channel in a direction substantially perpendicular to an axis of the shaft so as to secure the blade to said mounting block.

7. A retractor assembly according to claim 6, including a further plurality of blades of differing sizes or shapes forming a set wherein each blade is removably securable to the shaft thereby adapting the retractor shaft for positioning a diversity of tissue structures.

8. A retractor assembly according to claim 6, wherein the blade is formed of a radiolucent polymer.

9. A retractor assembly according to claim 6, wherein the shaft is adapted for longitudinal movement in a clamp channel of non-circular cross-sectional shape, and wherein the shaft has at least one elongated surface ridge such that the shaft rotates freely within a limited range in said channel for self alignment when contacting tissue and the shaft jams against the channel by interference of said ridge with said channel to automatically limit a range of rotation of the shaft.

10. A retractor assembly according to claim 9, wherein the shaft comprises four equi-spaced ridges and is configured to fit within a square channel of a clamp mechanism.

11. A retractor blade assembly for retracting tissue in a surgical arena, such retractor blade assembly comprising:

a shaft adapted for longitudinal movement within a passage of a clamping assembly carried on a ring, the shaft being adapted to carry a blade assembly at a distal end of the shaft for retracting tissue; and a blade assembly adapted to removably and replaceably mount at an end of the shaft by sliding in a dovetail groove in a direction substantially perpendicular to an axis of the shaft.

* * * * *